US006420473B1

(12) United States Patent
Chittamuru et al.

(10) Patent No.: US 6,420,473 B1
(45) Date of Patent: Jul. 16, 2002

(54) ACRYLIC ENTERIC COATING COMPOSITIONS

(75) Inventors: Ramireddy Chittamuru, Lansdale; George Reyes, Perkiomenville; Thomas P. Farrell, Warrington; Charles F. Vesey, Hatfield; Dev K. Mehra, Furlong, all of PA (US); Hans-Ulrich Petereit, Darmstadt; Klaus Lehmann, Rossdorf, both of (DE)

(73) Assignee: BPSI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/501,866

(22) Filed: Feb. 10, 2000

(51) Int. Cl.$^7$ .................................................. C08J 3/12
(52) U.S. Cl. ............................. 524/447; 424/33; 424/34
(58) Field of Search ............................. 524/447; 424/33, 424/34

(56) References Cited

U.S. PATENT DOCUMENTS

| 4,520,172 A | * | 5/1985 | Lehmann ..................... 525/369 |
| 4,543,370 A |   | 9/1985 | Porter et al. |
| 4,683,256 A |   | 7/1987 | Porter et al. |
| 4,855,402 A | * | 8/1989 | Salazar ........................ 528/487 |
| 5,725,880 A |   | 3/1998 | Hirakawa et al. |
| 5,733,575 A | * | 3/1998 | Mehra ......................... 424/480 |
| 5,914,132 A |   | 6/1999 | Kelm et al. |

OTHER PUBLICATIONS

Eudragit L 30 D Technical Application Pamphlet, date unknown*
Eudragit L 100–55 Technical Application Pamphlet, date unknown*

* cited by examiner

Primary Examiner—Paul R. Michl
(74) Attorney, Agent, or Firm—Roberts & Mercanti, LLP

(57) ABSTRACT

A non-toxic, edible, enteric film coating, dry powder composition for use in making an aqueous enteric suspension which may be used in coating pharmaceutical tablets comprises a) an acrylic resin, said resin comprising i) from 20 to 85 percent by weight of at least one alkyl acrylate or alkyl methacrylate moiety, ii) from 80 to 15 percent by weight of at least one vinyl or vinylidene moiety having a carboxylic acid group capable of salt formation, and iii) from 0 to 30 percent by weight of at least one other vinyl or vinylidene moiety copolymerizable with i) and ii), b) an alkalizing agent capable of reacting with the acrylic resin such that, after reaction, 0.1 to 10 mole percent of the acidic groups in 1a-ii) are present in the salt form, and c) a detackifier.

36 Claims, No Drawings

ACRYLIC ENTERIC COATING COMPOSITIONS

BACKGROUND OF THE INVENTION

1. Field of the Invention

This invention relates to the field of aqueous enteric film coating of pharmaceutical tablets and the like for preventing release of the ingredients of the coated tablet in the gastric juices of the stomach and for releasing the ingredients of the tablet in the intestines, and more particularly concerns providing a fully-formulated, non-toxic, edible, enteric, film-coating, dry powder composition based on an acrylic resin for use in making an aqueous enteric coating suspension that may be used in coating pharmaceuticals with an intestinally soluble coating that is insoluble in gastric juices of the stomach.

2. Description of the Prior Art

Several aqueous enteric film-coating systems are known. These include the AQUATERIC system, based on cellulose acetate phthalate, the SURETERIC system, based on polyvinylacetate phthalate (PVAP), and the EUDRAGIT L system, based on copolymers of acrylic acid esters and methacrylic acid. Both the AQUATERIC and EUDRAGIT L systems require at least three processing steps to form the enteric coating suspension. With the AQUATERIC system, the AQUATERIC powder is dispersed in water followed by stepwise addition of plasticizer Tween 80 and optional pigments to form the AQUATERIC suspension. The EUDRAGIT L system is available as a powder (L100-55) or as an aqueous dispersion (L30-D). The "EUDRAGIT L Technical Application Pamphlet (Info LD-13/e)" published by Rohm Pharma GmbH specifies a step-wise procedure to prepare an aqueous enteric dispersion which includes: 1) addition of the EUDRAGIT L100-55 powder to water; 2) dropwise addition of a pre-calculated amount of aqueous sodium hydroxide solution; 3) stirring of the dispersion for 30 minutes using a simple stirrer running at a medium and controllable speed; 4) filtration of the suspension; 5) subsequent addition of an aqueous solution of plasticizer (at a recommended use level of 10% by weight with respect to the EUDRAGIT L100-55 powder), "separating agent", and anti-foam to the filtered suspension; 6) further stirring; and 7) final filtration. Special precautions noted in this pamphlet include the warning that coagulation of the EUDRAGIT L aqueous dispersion may occur as a result of the presence of electrolytes, foam formation, exposure to heat and frost, the presence of finely divided pigments and exposure to high shear gradients when using fast-running stirrers and mills. Special attention is also drawn to the requirement to observe the specified formulation ratios, as a deviation could result in the formation of coagulum, which as set out in the pamphlet is "impossible" to redisperse rendering the entire aqueous dispersion "unusable."

The EUDRAGIT L30-D suspension is a dispersion of ethyl acrylate/methacrylic acid copolymer, 30% by weight in water. The "EUDRAGIT L Technical Application Pamphlet (Info LD-11 /e)" published by Rohm Pharma GmbH specifies a multi-step process for forming a complete aqueous dispersion system based on EUDRAGIT L30-D suspension that includes: 1) addition of plasticizer; 2) addition of a "separating agent"; 3) addition of an anti-foam; 4) optional addition of pigments; 5) stirring; and 6) final filtration. Special precautions, identical to those described for EUDRAGIT L100-55 powder, are also indicated in the EUDRAGIT L30-D suspension pamphlet.

The SURETERIC composition, which is described in Colorcon U.S. Pat. No. 5,733,575, which is incorporated herein by reference, advanced the art in the field by teaching the complete formulation of an enteric film coating pre-mix, which may be dispersed readily in water along with an anti-foam in two steps. The SURETERIC system requires the addition of a viscosity modifier to prevent settling of the suspended solids in the resulting aqueous dispersion during coating.

Lehmann et al. U.S. Pat. No. 4,520,172, which is incorporated herein by reference, discloses a binary mixture of EUDRAGIT L copolymer and a suitable alkalizing agent or "salt-forming agent." However, there are no known enteric film-coating systems based on the copolymer of ethyl acrylate and methyacrylic acid of the EUDRAGIT L system that are analogous to the SURETERIC system. Further, given the precautions cited in the Rohm Pharma literature and the chemical differences between PVAP and the methacrylic acid/ethyl acrylate copolymers, it would be surprising and unexpected if the Lehmann et al. binary system could be expanded into a fully-formulated solid composition which could then be dispersed readily in water for use in providing an enteric film coating.

SUMMARY OF THE INVENTION

It is an object of this invention to provide a fully-formulated, enteric film coating composition based on EUDRAGIT L copolymers that may be readily dispersed in water and applied to pharmaceutical tablets and the like.

Another object of this invention is to provide a fully formulated, enteric film coating composition based on EUDRAGIT L copolymers which does not cake upon preparation.

Another object of this invention is to provide a fully formulated, enteric film coating composition based on EUDRAGIT L copolymers which does not form agglomerates upon storage at elevated temperature and humidity.

Another object of this invention is to provide a fully-formulated, enteric film coating composition based on EUDRAGIT L copolymers which may be dispersed readily into water to form a coating dispersion that when applied to pharmaceutical tablets produces a tack-free coating.

Another object of this invention is to provide a fully formulated, enteric film coating composition, containing lake pigment and neutralizing agent, said lake pigment being stable upon dispersion in water.

Another object of this invention is to provide a fully-formulated, enteric film coating composition based on EUDRAGIT L copolymers which may be dispersed readily into water to form a coating dispersion that when applied to pharmaceutical tablets produces a film coating having an exceptional degree of film strength. This exceptional film strength is manifested by excellent performance in a "stressed disintegration test."

Another object of this invention is to provide a fully formulated, enteric film coating composition based on EUDRAGIT L copolymers that disperses in water without the formation of coagulum.

Another object of this invention is to reduce the number of steps in the preparation of aqueous film coating dispersions based on EUDRAGIT L copolymers from six (6) or more to two (2), thereby achieving the beneficial result of reducing the overall preparation time for preparing aqueous film coating dispersions from about 90 minutes to about 20 minutes.

These and other objects of the invention are accomplished by our invention, which is described below.

DETAILED DESCRIPTION OF THE INVENTION

In accordance with the invention, our non-toxic, edible, enteric film coating, dry powder composition for use in making an aqueous enteric suspension which may be used in coating pharmaceutical tablets comprises an acrylic resin (e.g., EUDRAGIT L copolymers), an alkalizing agent, and a detackifier. Optionally but advantageously, our dry powder composition may also include one or more of the following additives: a plasticizer; a pigment; a flow aid; a surfactant; an anti-agglomerating agent; a secondary film former; and a secondary detackifier. In a particularly preferred embodiment of this invention, the inventive dry powder composition contains an acrylic resin, an alkalizing agent, a detackifier, a plasticizer, a pigment, a flow aid, a surfactant, an anti-agglomerating agent, a secondary film-former and a secondary detackifier.

A method of making the inventive dry powder composition comprises the steps of mixing an acrylic resin with an alkalizing agent, detackifier, and optionally with one or more of the following additives: a plasticizer; a pigment; a flow aid; a surfactant; an anti-agglomerating agent; a secondary film former; and a secondary detackifier. The resulting enteric film coating dry powder composition and a separately-added anti-foam is readily dispersed in water, preferably deionized water, using a high shear mixer and is ready to use in 15–30 minutes. A high shear mixer is used rather than a slower stirrer to eliminate the formation of coagulum.

In accordance with the invention, a method of coating substrates, such as pharmaceutical tablets and the like, comprises mixing sequentially anti-foam and the inventive dry composition into water to form a coating suspension, applying the coating suspension onto the substrate to be coated to form a film coating on the substrates, and drying the film coating on the substrates.

The enteric polymer is an acrylic resin which comprises at least one vinyl or vinylidene moiety having a carboxylic acid group capable of salt formation. The acrylic resin may comprise of at least one vinyl or vinylidene moiety having a carboxylic acid group capable of salt formation and at least one alkyl acrylate or alkyl methacrylate moiety. The acrylic resin also may comprise of at least one vinyl or vinylidene moiety having a carboxylic acid group capable of salt formation, at least one alkyl acrylate or alkyl methacrylate moiety, and at least one other vinyl or vinylidene moiety copolymerizable with a) the alkyl acrylate or alkyl methacrylate moiety and b) the vinyl or vinylidene moiety having a carboxylic acid group capable of salt formation. Further, the acrylic resin may comprise of at least one vinyl or vinylidene moiety having a carboxylic acid group capable of salt formation and at least one other vinyl or vinylidene moiety copolymerizable with the vinyl or vinylidene moiety having a carboxylic acid group capable of salt formation.

Preferably, the enteric polymer is an acrylic resin which is comprised of: (1) from 20 to 85 percent by weight of at least one alkyl acrylate or alkyl methacrylate moiety; (2) from 80 to 15 percent by weight of at least one vinyl or vinylidene moiety having a carboxylic acid group capable of salt formation; and (3) from 0 to 30 percent by weight of at least one other vinyl or vinylidene moiety copolymerizable with (1) and (2). In a particularly preferred embodiment of this invention, the alkyl acrylate (1) is ethyl acrylate, and the vinyl moiety (2) is methacrylic acid. EUDRAGIT L100-55 powder is one example of a copolymer system meeting this definition.

Preferably, the acrylic resin comprises about 20% to about 80% by weight of the dry coating composition of the invention.

The alkalizing agent may be a bicarbonate, a carbonate, a phosphate, or a hydroxide of sodium or potassium, magnesium carbonate, magnesium hydroxide, ammonium carbonate, ammonium bicarbonate, magnesium oxide, calcium hydroxide, or mixtures thereof. The quantity of alkalizing agent used is directly dependent on the amount of carboxylic acid-bearing vinyl or vinylidene moiety present in the acrylic resin. Specifically, said alkalizing agent is added in a quantity such that, after reaction with the acrylic resin, 0.1 to 10 mole percent of the acidic groups are present in the salt form.

The detackifier may be talc, aluminum hydrate, glyceryl monostearate, kaolin, or mixtures thereof and is used principally to reduce the incidence of tablet-to-tablet sticking that can occur during the film coating of pharmaceutical tablets and the like using aqueous dispersions based on the inventive compositions. Preferably, the detackifier comprises about 5% to about 40% by weight of the dry coating composition of the invention.

The plasticizer may be triethylcitrate, glyceryltriacetate, acetyltriethylcitrate, dibutyl sebacate, diethylphthalate, polyethylene glycol having a molecular weight in the range of 200 to 8000, glycerol, castor oil, copolymers of propylene oxide and ethylene oxide, or mixtures thereof. When no plasticizer is included in the dry powder composition of the invention, the plasticizer is mixed separately into the coating suspension of the invention. Preferably, the plasticizer comprises 0% to about 20% by weight of the coating composition of the invention, and more preferably, the plasticizer comprises about 2% to about 20% by weight of the dry coating composition of the invention.

The pigment may be an FD&C or a D&C lake, titanium dioxide, magnesium carbonate, talc, pyrogenic silica, iron oxides, channel black, riboflavin, carmine 40, curcumin, annatto, insoluble dyes, pearlescent pigments based on mica and/or titanium dioxide or mixtures thereof. Other examples of suitable pigments are listed in Jeffries U.S. Pat. No. 3,149,040; Butler, et. al. U.S. Pat. No. 3,297,535; and Colorcon U.S. Pat. No. 3,981,984; all of which are incorporated herein by reference. The pigment may also include lake blends which contain a plasticizer and OPADRY pigmented coating compositions, some of which are disclosed in Colorcon U.S. Pat. No. 4,543,370, which is incorporated herein by reference. Preferably, the pigment comprises 0% to about 50% by weight of the inventive dry coating composition.

The flow aid may be silica such as fumed silica, supplied under the tradename Cab-O-Sil by Cabot, Inc. The flow aid imparts flowability to the powdered composition during dry blending and subsequent transferring from the blender to a storage container. Preferably, the flow aid comprises 0% to about 3% by weight of the inventive dry coating composition.

The surfactant may be sodium lauryl sulfate, dioctyl sodium sulfosuccinate, polysorbate 80, Tween 80, or mixtures thereof. Preferably, the surfactant comprises 0% to about 5% by weight of the inventive dry composition.

The anti-agglomerating agent may be kaolin. The quantity of anti-agglomerating agent in the inventive dry coating composition ranges from 0% to about 40% by weight of the inventive dry coating composition. Surprisingly, it has been found that relatively low levels of kaolin prevent clumping during preparation of the powdered composition and during storage of the final composition at elevated temperature and humidity. Preferably, kaolin is used at levels from greater than 0 percent to about 40% by weight of the composition. It has unexpectedly been found that a given level of kaolin imparts a much greater level of anti-agglomerating effect than the same amount of talc or silica, which are also known to be anti-agglomerating agents. Beneficially, kaolin serves both as an anti-agglomerating agent and a detackifier.

The secondary film former may be xanthan gum, sodium alginate, propylene glycol alginate, hydroxypropylmethylcellulose (HPMC), hydroxyethylecellulose (HEC), sodium carboxymethylcellulose (sodium CMC), polyvinylpyrrolidone (PVP), Konjac flour, carrageenan, other film-forming polymer or mixtures thereof. Preferably, the amount of secondary film former in the coating composition ranges from 0% to about 5% by weight of the dry coating composition of the invention. Use of the secondary film former improves the film strength of the inventive composition. Surprisingly, very low levels of a secondary film former can improve film strength as demonstrated by coating performance in the "stressed enteric test" developed by Colorcon. In a preferred embodiment of this invention, the incorporation of xanthan gum at a level of 0.5% by weight of the inventive composition resulted in superior stressed enteric test results when compared to a composition without xanthan gum.

The second detackifier may be sodium sulfate, calcium sulfate, calcium chloride, other inorganic or organic water-sequestering agents or mixtures thereof. Preferably, the amount of secondary detackifier in the coating composition ranges from 0% to about 5% by weight of the inventive dry coating composition of the invention. Surprisingly, incorporation of very low levels (greater than 0 to 5% by weight) of secondary detackifier results in a dramatic reduction of tablet tackiness, after being film-coated using the inventive aqueous dispersions in the most tackprone formulations. In a preferred embodiment of this invention, incorporation of calcium sulfate, at a level of only 0.15% by weight of the composition, results in the formation of tack-free tablets when coated with the inventive aqueous dispersions. Surprisingly, a given level of calcium sulfate or similar water-sequestering compound is much more effective in reducing coated tablet tack than identical levels of other known detackifiers such as talc and glyceryl monostearate. It is postulated that the secondary detackifier is functioning as a water-sequestering agent and binds free water on the tablet surface, preventing interaction of the water with the coalescing polymer, thereby effectively increasing the polymer glass transition temperature (Tg) and its resistance to further softening and attendant sticking to like tablets.

It is particularly advantageous to incorporate as many of the benefit-imparting additives of the inventive compositions into one formulation as possible. Therefore, a particularly preferred embodiment of this invention is the composition comprising: 1) an acrylic resin, preferably about 20 to about 80% by weight of the composition; 2) an alkalizing agent, present in an amount such that between about 0.1 to 10 mole % of the carboxylic acid groups on the acrylic resin will be neutralized; 3) a detackifier, preferably in the range of about 5% to about 40% by weight of the composition; 4) a plasticizer, preferably in the range of about 2% to about 20% by weight of the composition; 5) a pigment, preferably in the range of greater than 0% to about 50% by weight of the composition; 6) a flow aid, preferably in the range of greater than 0% to about 3% by weight of the composition; 7) a surfactant, preferably in the range of greater than 0% to about 5% by weight of the composition; 8) an anti-agglomerating agent, preferably in the range of greater than 0% to 40% by weight of the composition; 9) a secondary film former, preferably in the amount of greater than 0% to about 5% by weight of the composition; and 10) a secondary detackifier, preferably in the amount of greater than 0% to about 5% by weight of the composition.

It has been unexpectedly found that when said fully-formulated composition, containing lake pigments, is dispersed in water, the lake pigment is completely stable. That is no color bleeding is observed. This is particularly surprising in light of current industry art which dictates that colorants be added to the dispersion only after the neutralization step (acrylic polymer reacted with neutralizing agent) is complete in order to avoid "color bleeding."

A preferred method of preparing the inventive compositions is by conventional dry-blending using a "V-blender", food processor or similar device. Inventive compositions prepared by these conventional blending technologies are dispersed in aqueous solution prior to film-coating substrates, such as pharmaceutical tablets and the like, with the aid of a high shear mixer. Use of a high shear mixer allows the formation of a homogeneous aqueous dispersion without the formation of problematic coagulum. The following examples further illustrate the invention.

EXAMPLE 1

Aspirin cores (2.5 Kg total charge; 325 mg aspirin per tablet) were coated sequentially with a sub-coating dispersion made from a white Opadry® II coating composition (formula #574-39) and an enteric coating suspension prepared from the inventive composition. First, the Opadry II sub-coating dispersion was prepared by adding the dry Opadry II formula (50 grams) to deionized water (250 grams) and stirring this combination with a propeller mixer for 30 minutes. A homogeneous dispersion was thus obtained.

The inventive enteric, dry powder composition of this Example 1 was prepared by thoroughly mixing Eudragit® L100-55 powder (120.3 grams; 48.13 wt %), sodium bicarbonate (3.6 grams; 1.44 wt %), talc (57.3 grams; 22.93 wt %), Yellow#6 lake pigment (9.5 grams; 3.8 wt %), titanium dioxide (14.3 grams; 5.7 wt %), fumed silica (3.3 grams; 1.25 wt %), sodium lauryl sulfate (1.25 grams; 0.5 wt %), kaolin (12.5 grams; 5 wt %) and xanthan gum (0.625 grams; 0.25 wt %) in a food processor for five minutes. To this solid mixture was added triethylcitrate (27.5 grams; 11 wt %). After an additional two minutes of mixing, a homogeneous, free-flowing powder with no visible agglomerates was obtained.

The inventive enteric suspension was then prepared by first mixing Anti-foam FG-10 (1 gram) into deionized water (1.25 Kg) using a Silverson high-shear mixer (Model L-4RT-A) equipped with a general purpose dispersion head (i.e., GPDH ring) and operating at 1,500-2,000 RPM, with the stator placed in the center of vessel, for two minutes. The mixer stir rate was increased to 10,000 RPM, and the inventive enteric dry powder composition (250 grams) was added gradually to the vortex at a rate slow enough to avoid clumping (about one minute). After the addition was complete, the stator was placed off-center in the vessel to minimize air entrainment, and the suspension was further mixed at 10,000 RPM for an additional ten (10) minutes to yield a homogeneous, suspension with no visible agglomerates and no observable pigment degradation nor color bleeding.

To a 15 inch diameter O'Hara LabCoat 1 coating pan equipped with a Cole-Parmer Masterflex pump with one pump head, platinum-cured silicone tubing (size 15) and one Spraying Systems spray gun (⅛" VAU SS; fluid nozzle-VF60100-SS; air cap-VA1282125-60-SS), were added aspirin cores (2.5 Kg total charge; 325 mg of aspirin per tablet). The tablets were sequentially coated with the Opadry 11 sub-coating dispersion and the inventive, enteric coating suspension under the following process conditions:

| Coating Process Parameters (15" O'Hara LabCoat 1) | | |
| --- | --- | --- |
| | Subcoat | Enteric Coat |
| Fluid Delivery Rate (g/min) | 30 | 20 |
| Atomizing Air Pressure (psi) | 20 | 20 |
| Pattern Air Pressure (psi) | 30 | 30 |
| Tablet Bed Temperature (° C.) | 43 | 30 |
| Pan Speed (RPM) | 15 | 17 |

No tackiness or tablet-to-tablet sticking was observed during the coating run.

The final coated tablets were evaluated using USP Dissolution Method <711> according to the "delayed-release" aspirin monograph. As prescribed by this method, six tablets coated as described in Example 1 were placed in 0.1 N HCl for two hours at 37° C. The release in the acid phase of the test after two hours was 0.1%, as compared with the upper limit of 10%. The six tablets were then placed in phosphate buffer (pH=6.8), and the amount of aspirin released after 90 minutes was greater than 80% in 35 minutes, as compared to the compendial requirement of not less than 80% released after 90 minutes.

The final coated tablets were also evaluated using a modified version of USP Disintegration Method <701>. Fifty tablets prepared as described in Example 1 were stressed for 100 revolutions in a friabilator. Then, the 50 stressed tablets were placed in a basket assembly and immersed for one hour in simulated gastric fluid (0.1 N HCl). The basket was moved up and down in the simulated gastric fluid at a rate of about 28–32 cycles/minute. Fifty unstressed tablets were also placed in a basket assembly and immersed for one hour in simulated gastric fluid. The basket was moved up and down at a rate of about 28–32 cycles/min. The integrity of the tablets was evaluated after removal from the simulated gastric fluid. In both cases (stressed and unstressed), none of the tablets exhibited signs of bloating, cracks or fissures. The final coated tablets were also examined qualitatively. The resulting orange coating was smooth and uniform and showed no evidence of chipping, peeling or color non-uniformity.

EXAMPLES 2–5

Examples 2–5 are inventive compositions and inventive suspensions prepared in a manner analogous to the method described in Example 1 with slight adjustments to the composition as detailed in the following table. In all Examples 2–5, inventive compositions were free-flowing powders with no agglomerates, which when suspended in water, yielded suspensions with no visible coagulum and no observable pigment degradation or color bleeding. In all Examples 2–5, no tackiness was observed during the tablet-coating step. All tablets appeared smooth and uniform in both texture and color. Differences were noted in dissolution test performance as a function of xanthan gum content. The presence of xanthan gum in the formulas resulted in improved stressed dissolution test performance, which strongly suggests the film strength and imperviousness significantly increased when only very small quantities of xanthan gum were added.

| Comparative Data Table - Examples 2–5 | | | | |
| --- | --- | --- | --- | --- |
| | Wt % in 250 Grams | | | |
| Components | Example 2 | Example 3 | Example 4 | Example 5 |
| Eudragit ® L100-55 | 55.0 | 55.0 | 55.0 | 55.0 |
| Sodium bicarbonate | 1.65 | 1.65 | 1.65 | 1.65 |
| Talc | 20.1 | 20.6 | 24.6 | 16.0 |
| Kaolin | 5.0 | 5.0 | 5.0 | 5.0 |
| Titanium dioxide | 3.0 | 3.0 | 3.0 | 8.4 |
| Yellow#6 lake pigment | 2.0 | 2.0 | 2.0 | 5.6 |
| Sodium lauryl sulfate | 0.5 | 0.5 | 0.5 | 0.5 |
| Fumed Silica | 1.25 | 1.25 | 1.25 | 1.25 |
| Triethylcitrate | 11.0 | 11.0 | 6.5 | 6.5 |
| Xanthan Gum | 0.5 | 0.0 | 0.5 | 0.0 |
| % Passed | 100% | 100% | 100% | 100% |
| Standard Disintegration Test | 100 | 100 | 100 | 100 |
| Stressed Disintegration Test | 98 | 90 | 84 | 28 |

EXAMPLES 6–9

Examples 6–9 are inventive compositions and inventive suspensions prepared in a manner analogous to the method described in Example 1 with slight adjustments to the composition as detailed in the following table. In Examples 6–9, inventive compositions were free-flowing powders with no agglomerates, which when suspended in water, yielded suspensions with no visible coagulum and no observable pigment degradation or color bleeding. During the tablet coating step of Examples 6–9, the tablet bed temperature was 32–35° C., in contrast to the bed temperature of 30° C. maintained in Examples 1–5. Generally, propensity toward tackiness increases with increasing bed temperature. In Example 6, some tackiness and tablet-to-tablet sticking was observed in the tablet coating step. In Examples 7–9, no tackiness was observed during the tablet coating step. The propensity towards tackiness at elevated bed temperature was offset by the addition of very small quantities of a secondary detackifier (sodium sulfate, calcium sulfate dihydrate or calcium chloride). Upon completion of the coating runs, all tablets appeared smooth and uniform in both texture and color.

Comparative Data Table - Examples 6–9

| Components | Example 6 | Example 7 | Example 8 | Example 9 |
|---|---|---|---|---|
| Eudragit ® L100-55 | 49.0 | 49.0 | 49.0 | 49.0 |
| Sodium bicarbonate | 1.45 | 1.47 | 1.47 | 1.47 |
| Talc | 25.45 | 25.3 | 25.3 | 25.3 |
| Kaolin | 5.0 | 5.0 | 5.0 | 5.0 |
| Titanium dioxide | 5.82 | 5.82 | 5.82 | 5.82 |
| Yellow#6 lake pigment | 3.88 | 3.88 | 3.88 | 3.88 |
| Sodium lauryl sulfate | 0.5 | 0.5 | 0.5 | 0.5 |
| Fumed Silica | 1.30 | 1.28 | 1.28 | 1.28 |
| Triethylcitrate | 7.6 | 7.6 | 7.6 | 7.6 |
| Sodium sulfate | 0.0 | 0.15 | 0.0 | 0.0 |
| Calcium sulfate dihydrate | 0.0 | 0.0 | 0.15 | 0.0 |
| Calcium chloride | 0.0 | 0.0 | 0.0 | 0.15 |
|  | 100% | 100% | 100% | 100% |
| Tackiness during Coating | YES | NO | NO | NO |
| % Passed Std Dissolution Test | 100 | 100 | 100 | 100 |

EXAMPLES 10 & 11

Examples 10 and 11 are inventive compositions and inventive suspensions prepared in a manner analogous to the method described in Example 1 except iron oxide-based colorants were used. In Examples 10 and 11, inventive compositions were free-flowing powders with no agglomerates, which when suspended in water, yielded suspensions with no visible coagulum and no observable color bleeding. In Examples 10 and 11, no tackiness was observed during the tablet-coating step. All tablets appeared smooth and uniform in both texture and color.

Comparative Data Table - Examples 10 and 11

| Components | Example 10 | Example 11 |
|---|---|---|
| Eudragit ® L100-55 | 50.0 | 50.0 |
| Sodium bicarbonate | 1.50 | 1.50 |
| Talc | 26.25 | 26.25 |
| Kaolin | 5.0 | 5.0 |
| Titanium dioxide | 5.1 | 5.1 |
| Red iron oxide | 3.4 | 0.0 |
| Yellow iron oxide | 0.0 | 3.4 |
| Sodium lauryl sulfate | 0.5 | 0.5 |
| Fumed Silica | 1.25 | 1.25 |
| Triethylcitrate | 7.0 | 7.0 |
|  | 100% | 100% |
| Tablet Color | Red | Yellow |
| Standard Disintegration Test (% Passed) | 98 | 100 |

EXAMPLES 12–15

Examples 12–15 are inventive compositions and inventive suspensions prepared in a manner analogous to the method described in Example 1 with some changes to the formula as detailed in the following table. When kaolin was included in the formula, there was no evidence of caking or agglomerate formation in the powder. In contrast, formulas, which contained talc but no kaolin, did show significant caking and agglomerate formation in the powder. The formulations of Examples 12 to 15 were tested for color bleeding, and the test results showed no evidence of color bleeding in the aqueous suspensions prepared from the inventive compositions both at "time zero" and after storage of the powder compositions for one month at 40° C. and 75% relative humidity. All tablets appeared smooth and uniform in both texture and color.

Comparative Data Table - Examples 12–15

| Components | Example 12 | Example 13 | Example 14 | Example 15 |
|---|---|---|---|---|
| Eudragit ® L100-55 | 55.0 | 55.0 | 49.0 | 49.0 |
| Sodium bicarbonate | 1.76 | 1.76 | 1.57 | 1.57 |
| Talc | 30.0 | 0.0 | 27.0 | 0.0 |
| Kaolin | 0.0 | 30.0 | 0.0 | 27.0 |
| Titanium dioxide | 0.0 | 0.0 | 5.82 | 5.82 |

-continued

Comparative Data Table - Examples 12–15

| | Wt % in 250 Grams | | | |
|---|---|---|---|---|
| Components | Example 12 | Example 13 | Example 14 | Example 15 |
| Yellow#6 Lake Pigment | 0.0 | 0.0 | 3.88 | 3.88 |
| Sodium lauryl sulfate | 0.5 | 0.5 | 0.5 | 0.5 |
| Glyceryl monostearate | 1.6 | 1.6 | 1.5 | 1.5 |
| Tween ® 80 | 2.2 | 2.2 | 2.0 | 2.0 |
| Fumed Silica | 0.94 | 0.94 | 0.73 | 0.73 |
| Triethylcitrate | 8.0 | 8.0 | 8.0 | 8.0 |
| | 100% | 100% | 100% | 100% |
| Agglomerate Formation | | | | |
| Upon powder preparation | YES | NO | YES | NO |
| After powder storage for 1 month at 40° C./75% RH | YES | NO | YES | NO |
| Tablet Color | White | White | Orange | Orange |
| Standard Disintegration Test (% Passed) | 96 | 100 | 98 | 94 |

EXAMPLES 16–18

Examples 16–18 are inventive compositions and inventive suspensions prepared in a manner analogous to the method described in Example 1 with some changes to the formula as detailed in the following table. When kaolin was included in the formula, there was no evidence of caking or agglomerate formation in the powder. In contrast, formulas, which contained talc but no kaolin, did show significant caking and agglomerate formation in the powder. There was no evidence of color bleeding in the aqueous suspensions prepared from the inventive compositions both at "time zero" and after storage of the powder compositions for one month at 40° C. and 75% relative humidity. All tablets appeared smooth and uniform in both texture and color. In Example 18, elimination of glyceryl monostearate, sodium lauryl sulfate and Tween 80 from the formula resulted in the production of coated tablets that had much less gloss or sheen than those of Examples 16 and 17.

Comparative Data Table - Examples 16–18

| | Wt % in 250 Grams | | |
|---|---|---|---|
| Components | Example 16 | Example 17 | Example 18 |
| Eudragit ® L100-55 | 49.0 | 49.0 | 49.0 |
| Sodium diphosphate (anhydrous) | 1.65 | 1.65 | 1.65 |
| Talc | 27.0 | 0.0 | 0.0 |
| Kaolin | 0.0 | 27.0 | 31.9 |
| Titanium dioxide | 5.82 | 5.82 | 5.82 |
| Yellow#6 Lake Pigment | 3.88 | 3.88 | 3.88 |
| Sodium lauryl sulfate | 0.5 | 0.5 | 0.0 |
| Glyceryl monostearate | 1.5 | 1.5 | 0.0 |
| Tween ® 80 | 2.0 | 2.0 | 0.0 |
| Fumed Silica | 0.9 | 0.9 | 0.0 |
| Triethylcitrate | 7.75 | 7.75 | 7.75 |
| | 100% | 100% | 100% |
| Agglomerate Formation | | | |
| Upon powder preparation | YES | NO | NO |
| After powder storage for 1 month at 40° C./75% RH | YES | NO | N/A |
| Tablet Color/Appearance | Orange/Shiny | Orange/Shiny | Orange/Dull |
| Standard Disintegration Test (% Passed) | 94 | 98 | 92 |

EXAMPLES 19–26

Examples 19–26 are inventive compositions and inventive suspensions prepared in a manner analogous to the method described in Example 1 except that significant adjustments were made to the formulation, and the powder preparation (100 grams), suspension preparation (500 grams) and coating process (12" diameter pan; 1 Kg charge of aspirin cores) were scaled down.

Comparative Data Table - Examples 19–22

| Components | Wt % in 100 Grams | | | |
|---|---|---|---|---|
| | Example 19 | Example 20 | Example 21 | Example 22 |
| Eudragit ® L100-55 | 60.0 | 60.0 | 60.0 | 60.0 |
| Sodium bicarbonate | 1.8 | 1.8 | 1.8 | 1.8 |
| Talc | 38.2 | 31.0 | 28.5 | 36.9 |
| Kaolin | 0.0 | 0.0 | 0.0 | 0.0 |
| Titanium dioxide | 0.0 | 0.0 | 5.82 | 0.0 |
| Yellow#6 lake pigment | 0.0 | 0.0 | 3.88 | 0.0 |
| Sodium lauryl sulfate | 0.0 | 0.0 | 0.0 | 0.0 |
| Fumed Silica | 0.0 | 0.0 | 0.0 | 1.3 |
| Triethylcitrate | 0.0 | 7.2 | 0.0 | 0.0 |
| Calcium sulfate dihydrate | 0.0 | 0.0 | 0.0 | 0.0 |
| Xanthan Gum | 0.0 | 0.0 | 0.0 | 0.0 |
| % Passed | 100% | 100% | 100% | 100% |
| Standard Disintegration Test | 98 | 100 | 2 | 98 |
| Stressed Disintegration Test | 0 | 2 | 0 | 0 |
| Tablet Color/Appearance | White/Dull | White/Shiny | Orange/Dull | White/Dull |

Comparative Data Table - Examples 23–26

| Components | Wt % in 100 Grams | | | |
|---|---|---|---|---|
| | Example 23 | Example 24 | Example 25 | Example 26 |
| Eudragit ® L100-55 | 60.0 | 60.0 | 60.0 | 60.0 |
| Sodium bicarbonate | 1.8 | 1.8 | 1.8 | 1.8 |
| Talc | 37.7 | 33.2 | 37.7 | 38.05 |
| Kaolin | 0.0 | 5.0 | 0.0 | 0.0 |
| Titanium dioxide | 0.0 | 0.0 | 0.0 | 0.0 |
| Yellow#6 lake pigment | 0.0 | 0.0 | 0.0 | 0.0 |
| Sodium lauryl sulfate | 0.5 | 0.0 | 0.0 | 0.0 |
| Fumed Silica | 0.0 | 0.0 | 0.0 | 0.0 |
| Triethylcitrate | 0.0 | 0.0 | 0.0 | 0.0 |
| Calcium sulfate dihydrate | 0.0 | 0.0 | 0.0 | 0.15 |
| Xanthan Gum | 0.0 | 0.0 | 0.5 | 0.0 |
| % Passed | 100% | 100% | 100% | 100% |
| Standard Disintegration Test | 98 | 96 | 94 | 100 |
| Stressed Disintegration Test | 0 | 0 | 2 | 0 |
| Tablet Color/Appearance | White/Dull | White/Dull | White/Dull | White/Dull |

What is claimed is:

1. A non-toxic, edible, enteric film coating, dry powder composition for use in making an aqueous enteric suspension which may be used in coating pharmaceutical tablets comprising
   a) an acrylic resin, said resin comprising
      i) from 20 to 85 percent by weight of at least one alkyl acrylate or alkyl methacrylate moiety,
      ii) from 80 to 15 percent by weight of at least one vinyl or vinylidene moiety having a carboxylic acid group capable of salt formation, and
      iii) from 0 to 30 percent by weight of at least one other vinyl or vinylidene moiety copolymerizable with i) and ii),
   b) an alkalizing agent capable of reacting with the acrylic resin such that, after reaction, 0.1 to 10 mole percent of the acidic groups in 1a-ii) are present in the salt form, and
   c) a film coating detackifier.

2. The enteric film coating dry powder composition of claim 1, further including a plasticizer.

3. The enteric film coating dry powder composition of claim 1, further including a pigment.

4. The enteric film coating dry powder composition of claim 1, further including a flow aid.

5. The enteric film coating dry powder composition of claim 1, further including a surfactant.

6. The enteric film coating dry powder composition of claim 1, further including an anti-agglomerating agent.

7. The enteric film coating dry powder composition of claim 1, further including a secondary film former.

8. The enteric film coating dry powder composition of claim 1, further including a secondary detackifier.

9. The enteric film coating dry powder composition of claim 1, the alkyl acrylate being ethyl acrylate and the vinyl or vinylidene moiety having a carboxylic acid group capable of salt formation being methacrylic acid.

10. The enteric film coating dry powder composition of claim 1, the alkalizing agent (b) being a bicarbonate, a carbonate, a phosphate, or a hydroxide of sodium or potassium, magnesium carbonate, magnesium hydroxide, ammonium carbonate, ammonium bicarbonate, magnesium oxide, calcium hydroxide, or mixtures thereof.

11. The enteric film coating dry powder composition of claim 1, the film coating detackifier being talc, aluminum hydrate, glyceryl monostearate, kaolin, or mixtures thereof.

12. The enteric film coating dry powder composition of claim 2, the plasticizer being triethylcitrate, glyceryltriacetate, acetyltriethylcitrate, dibutyl sebacate, diethylphthalate, polyethylene glycol having a molecular weight in the range of 200 to 8000, glycerol, castor oil, copolymers of propylene oxide and ethylene oxide, or mixtures thereof.

13. The enteric film coating dry powder composition of claim 3, the pigment being FD&C and D&C lakes, titanium dioxide, magnesium carbonate, talc, pyrogenic silica, iron oxides, channel black, riboflavin, carmine 40, curcumin, annatto, insoluble dyes, pearlescent pigments based on mica and/or titanium dioxide or mixtures thereof.

14. The enteric film coating dry powder composition of claim 4, the flow aid being silica.

15. The enteric film coating dry powder composition of claim 5, the surfactant being sodium lauryl sulfate, dioctyl sodium sulfosuccinate, polysorbate 80, Tween 80 or mixtures thereof.

16. The enteric film coating dry powder composition of claim 6, the anti-agglomeration agent being kaolin.

17. The enteric film coating dry powder composition of claim 7, the secondary film former being xanthan gum, sodium alginate, propylene glycol alginate, hydroxypropylmethylcellulose (HPMC), hydroxyethylecellulose (HEC), sodium carboxymethylcellulose (sodium CMC), polyvinylpyrrolidone (PVP), Konjac flour, carrageenan, other film-forming polymer or mixtures thereof.

18. The enteric film coating dry powder composition of claim 8, the secondary detackifier being sodium sulfate, calcium sulfate, calcium chloride, other inorganic or organic water-sequestering agents or mixtures thereof.

19. The enteric film coating dry powder composition of claim 9, further including a plasticizer, a pigment, a flow aid, a surfactant, an anti-agglomerating agent, a secondary film former, and a secondary detackifier, the acrylic resin being in a range of about 20 to about 80 percent by weight of the composition, the alkalizing agent being a bicarbonate, a carbonate, a phosphate, or a hydroxide of sodium or potassium, magnesium carbonate, magnesium hydroxide, ammonium carbonate, ammonium bicarbonate, magnesium oxide, calcium hydroxide, or mixtures thereof, the detackifier being talc, aluminum hydrate, glyceryl monostearate, kaolin, or mixtures thereof, the detackifier being in the range of about 5% to about 40% by weight of the composition, the plasticizer being triethylcitrate, glyceryltriacetate, acetyltriethylcitrate, dibutyl sebacate, diethylphthalate, polyethylene glycol having a molecular weight in the range of 200 to 8000, glycerol, castor oil, copolymers of propylene oxide and ethylene oxide, or mixtures thereof, the plasticizer being in the range of about 2% to about 20% by weight of the composition, the pigment being FD&C and D&C lakes, titanium dioxide, magnesium carbonate, talc, pyrogenic silica, iron oxides, channel black, riboflavin, carmine 40, curcumin, annatto, insoluble dyes, pearlescent pigments based on mica and/or titanium dioxide or mixtures thereof, the pigment being in the range of greater than 0% to about 50% by weight of the composting, the following aid being silica, the flow aid being in the range of greater than 0% to about 3% by weight of the composition, the surfactant being sodium lauryl sulfate, dioctyl sodium sulfosuccinate, polysorbate 80, Tween 80 or mixtures thereof, the surfactant being in the range of greater than 0% to about 5% by weight of the composition, the anti-agglomerating agent being kaolin, the anti-agglomerating agent being present in the range of greater than 0% to about 40% by weight of the composition, the secondary film former being xanthan gum, sodium alginate, propylene glycol alginate (PGA), hydroxypropylmethylcellulose (HPMC), hydroxyethylecellulose (HEC), sodium carboxymethylcellulose (sodium CMC), polyvinylpyrrolidone (PVP), Konjac flour, carrageenan, other film-forming polymer or mixtures thereof, the secondary film former being present in the amount of greater than 0% to about 5% by weight of the composition, the secondary detackifier being sodium sulfate, calcium sulfate, calcium chloride, other inorganic or organic water-sequestering agents or mixtures thereof, and the secondary detackifier being present in the amount of greater than 0% to about 5% by weight of the composition.

20. A non-toxic, edible, enteric film coating, dry powder composition for use in making an aqueous enteric suspension which may be used in coating pharmaceutical tablets comprising a) an acrylic resin, said resin comprising
  i) from 15 to 80 percent by weight of at least one vinyl or vinylidene moiety having a carboxylic acid group capable of salt formation, and
  ii) from 20 to 85 percent by weight of at least one other vinyl or vinylidene moiety copolymerizable with i), b) an alkalizing agent capable of reacting with the acrylic resin such that, after reaction, 0.1 to 10 mole percent of the acidic groups in 1a-i) are present in the salt form, and c) a film coating detackifier.

21. The composition of claim 20, further including a plasticizer, a pigment, a flow aid, a surfactant, an anti-agglomerating agent, a secondary film former, a secondary detackifier, or a combination thereof.

22. A non-toxic, edible, enteric film coating, dry powder composition for use in making an aqueous enteric suspension which may be used in coating pharmaceutical tablets comprising a) an acrylic resin comprising at least one vinyl or vinylidene moiety having a carboxylic acid group capable of salt formation, b) an alkalizing agent capable of reacting with the acrylic resin such that, after reaction, 0.1 to 10 mole percent of the acidic groups of the vinyl or vinylidene moiety are present in the salt form, and c) a film coating detackifier.

23. The composition of claim 22, further including a plasticizer, a pigment, a flow aid, a surfactant, an anti-aglomerating agent, a secondary film former, a secondary detacktifier, or a combination thereof.

24. A method of making an aqueous coating dispersion for use in pharmaceuticals, confectionery and food, comprising the steps of (a) dry blending an acrylic resin, an alkalizing agent, and a film coating detackifier to form a non-toxic, edible, enteric film coating, dry powder composition, (b) adding the dry powder composition of step a) to water, and (c) stirring said dry powder composition in water using a high-shear mixer or similar apparatus to form an aqueous coating suspension.

25. The method of claim 24, further including mixing a plasticizer, a pigment, a flow aid, a surfactant, an anti-agglomerating agent, a secondary film former, a secondary detackifier, or a combination thereof with the acrylic resin, the alkalizing agent, and the detackier to form the non-toxic, edibe, enteric film coating, dry powder composition.

26. A method of coating substrates such as pharmaceutical tablets and the like with a film coating comprising the steps of mixing an acrylic resin, an alkalizing agent, and a film coating detackifier together to form a non-toxic, edible, enteric film coating, dry powder composition, mixing the composition into water to form an aqueous coating suspension, applying an effective amount of said coating suspension onto said substrates to form a film coating on said substrates, and drying the film coating on said substrates.

27. The method of claim 26, further including mixing a plasticizer, a pigment, a flow aid, a surfactant, an anti-agglomerating agent, a secondary film former, a secondary detackifier, or a combination thereof with the acrylic resin, the alkalizing agent, and the detackifier to form the non-toxic, edible, enteric film coating, dry powder composition.

28. The non-toxic, edible enteric film coating, dry powder composition of claim 20, wherein the film coating detackifier is selected from the group consisting of talc, aluminum hydrate, glyceryl monostearate, kaolin and mixtures thereof.

29. The non-toxic, edible, enteric film coating, dry powder composition of claim 22, wherein the film coating detackifier is selected from the group consisting of talc, aluminum hydrate, glyceryl monostearate, kaolin and mixtures thereof.

30. The method of claim 24, wherein the film coating detackifier is selected from the group consisting of talc, aluminum hydrate, glyceryl monostearate, kaolin and mixtures thereof.

31. The method of claim 26, wherein the film coating detackifier is selected from the group consisting of talc, aluminum hydrate, glyceryl monostearate, kaolin and mixtures thereof.

32. The composition of claim 1, wherein the film coating detackifier comprises from about 5% to about 40% of the composition.

33. The composition of claim 20, wherein the film coating detackifier comprises from about 5% to about 40% of the composition.

34. The composition of claim 22, wherein the film coating detackifier comprises from about 5% to about 40% of the composition.

35. The method of claim 24, wherein the film coating detackifier comprises from about 5% to about 40% of the composition.

36. The method of claim 26, wherein the film coating detackifier comprises from about 5% to about 40% of the composition.

* * * * *

UNITED STATES PATENT AND TRADEMARK OFFICE
CERTIFICATE OF CORRECTION

PATENT NO.     : 6,420,473 B1
DATED          : July 16, 2002
INVENTOR(S)    : Ramireddy Chittamuru et al.

It is certified that error appears in the above-identified patent and that said Letters Patent is hereby corrected as shown below:

Title page,
Item [73], after "BPSI Holdings, Inc., Wilmington, DE (US)" insert -- and Röhm GmbH & Co. KG, Chemische Fabrik, Darmstadt, Germany (DE) --.

Column 15,
Line 37, delete "anti-agglomeration" and substitute therefor -- anti-agglomerating --.

Column 16,
Line 18, delete "composting" and substitute therefor -- composition --.
Line 19, delete "following" and substitute therefor -- flow --;

Column 17,
Lines 14-15, delete "anti-aglomerating" and substitute therefor -- anti-agglomerating --.
Line 34, delete "edibe" and substitute therefor -- edible --.

Signed and Sealed this

First Day of July, 2003

JAMES E. ROGAN
*Director of the United States Patent and Trademark Office*